US007828205B2

United States Patent
Cronin et al.

(10) Patent No.: US 7,828,205 B2
(45) Date of Patent: Nov. 9, 2010

(54) METHOD OF PROMOTING HEALTH AND WELLNESS THROUGH CARD BASED REWARDS PROGRAM

(75) Inventors: Eugene Cronin, Avon, CT (US); Christine Skelly, West Hartford, CT (US)

(73) Assignee: Aetna Inc., Hartford, CT (US)

( * ) Notice: Subject to any disclaimer, the term of this patent is extended or adjusted under 35 U.S.C. 154(b) by 890 days.

(21) Appl. No.: 11/676,844

(22) Filed: Feb. 20, 2007

(65) Prior Publication Data

US 2008/0197185 A1 Aug. 21, 2008

(51) Int. Cl.
G06K 5/00 (2006.01)
G06F 17/00 (2006.01)
(52) U.S. Cl. ...................................... 235/380; 235/375
(58) Field of Classification Search .................. 235/380, 235/375, 382, 383, 385, 492, 481
See application file for complete search history.

(56) References Cited

U.S. PATENT DOCUMENTS

| 7,493,266 | B2 * | 2/2009 | Gupta ............................ 705/3 |
| 2002/0147678 | A1 * | 10/2002 | Drunsic ....................... 705/39 |
| 2002/0156731 | A1 * | 10/2002 | Seki et al. ..................... 705/40 |
| 2002/0194131 | A1 * | 12/2002 | Dick ............................ 705/51 |
| 2003/0187694 | A1 | 10/2003 | Rowen |
| 2004/0107134 | A1 * | 6/2004 | Nelson et al. ................. 705/14 |
| 2005/0075909 | A1 | 4/2005 | Flagstad |
| 2005/0149425 | A1 * | 7/2005 | Hagan .......................... 705/36 |
| 2005/0234742 | A1 * | 10/2005 | Hodgdon ....................... 705/2 |
| 2006/0064320 | A1 * | 3/2006 | Postrel ........................... 705/2 |
| 2009/0192876 | A1 * | 7/2009 | De et al. ....................... 705/10 |

OTHER PUBLICATIONS

Article entitled "Citibank and Royal Sundaram launch co-branded credit card in India," Insurance Business Review ONLINE, dated Jan. 13, 2006; retrieved Aug. 24, 2006 from http://www.insurance-business-review.com/article_news_print.asp?g (2 pages).

(Continued)

*Primary Examiner*—Thien M Le
(74) *Attorney, Agent, or Firm*—Leydig, Voit & Mayer, Ltd.

(57) ABSTRACT

A system and method are described whereby a health care organization (HCO) cooperates with a financial organization by promoting enrollment and use of a financial product or service that includes terms having incentives related to health care expenditures. In one embodiment, the financial product or service is a credit card program including incentives related to health care expenses. The HCO identifies and selects a group of consumers suitable to receive promotional information related to the credit card program. Preferably, the credit card program is associated with the HCO via a co-branding arrangement. The HCO obtains revenue from the financial organization based on consumer's use of the credit card and, optionally, based on new enrollments. Although a consumer can use the credit card to pay for any product or service, the incentives are applied when the card is used in connection with products or services related to health care.

19 Claims, 4 Drawing Sheets

OTHER PUBLICATIONS

Article entitled "Delayed Epiphany," dated Feb. 24, 2006; retrieved Aug. 21, 2006 from http://delayedepiphany.blogspot.com/2006/02/ways-to-save.html (3 pages).

Web pages entitled Royal Sundaram Citibank Gold Card; no stated date but no later than applicants' filing date; retrieved Aug. 24, 2006 from https://wvvw.online.citibank.co.in/portal/generic.jsp?sgringID-newg (4 pages).

Article entitled "Summary of the HIPAA Privacy Rule," last revised May 2003, United States Department of Health & Human Services—Office of Civil Rights—HIPAA web site, General Background Information, Privacy Rule Summary, on Sep. 29, 2006 at http://www.hhs.gov/ocr/hipaa/ (25 pages).

Article entitled "Marketing," revised Apr. 3, 2003, United States Department of Health & Human Services—Office of Civil Rights—HIPAA web site; retrieved on Sep. 29, 2006 at http://www.hhs.gov/ocr/hipaa/privacy.html (4 pages).

* cited by examiner

METHOD OF PROMOTING HEALTH AND WELLNESS THROUGH CARD BASED REWARDS PROGRAM

FIELD OF THE INVENTION

This invention relates generally to the field of financial products and services and more specifically to the area of consumer credit cards.

BACKGROUND OF THE INVENTION

Modern health care consumers must frequently face a dichotomy between the need for continued access to health care and the need to control the growth of health care expenses. While a number of options exist that help alleviate the growing health care expenditures, many such options have inherent limits. For example, Flexible Spending Arrangements (FSA) and Health Reimbursement Arrangements (HRA) help reduce the consumers' costs of health care related spending that is not covered by health, dental, or vision insurance by allowing tax-free savings to be allocated for future health care expenditures. However, not all consumers have access to these options because employer participation in these plans is a necessary prerequisite and, at least in the case of the FSA, only a fixed amount of consumer's pre-tax dollars is eligible for participation. Therefore, consumers that are not able to take advantage of the FSA/HRA type arrangements, as well as consumers that incur health care expenses well above the predefined tax-free limits or that otherwise are not covered by insurance, are forced to rely on personal savings or other financial products, such as loans and credit cards to pay for the balance of their health care expenses. For some consumers, this acts as a disincentive to continue receiving the same quality of health care services and, therefore, may lead to a decline in personal health.

On the other hand, maintaining and improving the personal health of their consumers is of primary concern to certain health care organizations, including health insurance companies, for example. Therefore, health care organizations have an interest in promoting health care, including helping the consumers pay for the growing health care expenses, and a need to identify the consumers which may respond in a positive way. While many health care organizations have extensive records collected in the process of providing health care products and services, use of such information is regulated in order to safeguard the consumer privacy. For example, the Health Insurance Portability and Accountability Act (HIPAA) and the associated regulations require an authorization to use and disclose individually identifiable health information, unless such information is used in connection with providing health related products or services.

BRIEF SUMMARY OF THE INVENTION

In embodiments of the invention, in order to improve health and wellness and to alleviate increasing costs of medical expenses for its consumers, a health care organization (HCO) cooperates with a financial organization by promoting enrollment and use of a financial product or service that includes terms having incentives for the use of the product or service in connection with health care. In certain embodiments, the financial organization is a bank. In such an embodiment, the financial product or service is a credit card program having at least one credit card, which includes an account with an interest rate that applies to balances carried on the account, and including one or more incentives to use the credit card in connection with health care expenses. The HCO queries its consumer database, and, using the private health information of its consumers, it identifies and selects a group of health care consumers suitable to receive promotional information related to the credit card program. Once the HCO identifies a group of consumers that are suitable to receive the promotional information, the HCO uses one or more of its channels of communication to transmit the promotional information to the select group. In one embodiment, the HCO transmits the promotional information relating to the credit card program via the Internet, telephone, and mail channels. Preferably, the credit card program is associated with the HCO via a co-branding arrangement, whereby the promotional materials, as well as the credit card, include a logo of the HCO and, optionally, other brand information related to the HCO.

In an embodiment, upon receipt of the promotional information, the consumer applies for the credit card program by sending a credit card application, which was included or referenced in the promotional information, to the financial organization for processing. Upon approval of the application, the financial organization assigns to the consumer an account number and stores the account details in an account database. The HCO, in turn, obtains revenue from the financial organization based on consumer's use of the credit card, where the revenue is preferably measured as a predetermined percentage of the consumer's transaction amount. In another embodiment, the HCO obtains additional revenue from the financial organization based on new enrollments in the credit card program resulting from the selected group of consumers.

Although a consumer can use the credit card to pay for any product or service, the card includes special incentives to benefit the consumer when the card is used in connection with products or services related to health care. In one embodiment, upon approval of the transaction request, the financial organization receives a merchant category code from a merchant and determines whether the code is associated with a category indicating that many or all products or services provided by the merchant are related to health care. If so, the financial organization applies one or more incentives to the transaction.

In embodiments, the health care incentives may include a reward program where the consumer earns reward units or points upon using the credit card to make purchases. In one embodiment, the reward program includes a reward unit discount allowing the consumer to reduce the amount of accumulated reward units necessary for redeeming merchandise when such reward units are earned in connection with health care related purchases. Preferably, a reward unit discount also applies when the consumer is redeeming rewards that are related to health care. Another embodiment of a reward program includes a provision that increases the number of reward units awarded in connection with the purchase of products or services related to health care as compared to non-healthcare related purchases. Similarly, the incentives may include an interest rate reduction applicable to charges generated by paying for health care products or services. In yet another embodiment, the financial organization applies a predetermined discount applicable to health care related purchases. The discount may take the form of a predetermined percent discount or a cash rebate based on a total amount of health care related charges.

In one aspect of the invention, a method is provided for promoting a financial product or service by a person or organization in possession of private health information related to a plurality of consumers, the method comprising determining that the financial product or service has terms that relate to health care, using the private health information to identify and select a group of the consumers as suitable to receive promotional information related to the financial product or service, and transmitting the promotional information to consumers of the select group.

In another aspect of the invention, a method is provided for promoting a credit card program by a person or organization in possession of private health information related to a plurality of consumers, the credit card program having at least one credit card having an account with an interest rate that applies to balances carried on the account, the method comprising determining that at least one term of the credit card program relates to health care, the term comprising incentives for use of the credit card program in connection with products or services related to health care, the incentives selected from the group consisting of (a) a reward program having a reward unit discount that applies for redeeming rewards for the products or services related to health care, (b) a reduction in the interest rate when the credit card is used to pay for the products or services related to health care, (c) a discount that applies when the credit card is used to pay for the products or services related to health care, and (d) a reward program that awards reward units in connection with consumer purchases and having a provision that increases the number of reward units awarded in connection with the purchase of products or services related to health care; using the private health information to identify and select a group of the consumers as suitable to receive promotional information related to the credit card program, and transmitting the promotional information to consumers of the select group.

In yet another aspect of the invention, a method is provided for commercializing a financial product or service, the method comprising establishing terms for the financial product or service, at least one of the terms relating to health care, offering the financial product or service to be promoted by a person or organization that is in the possession of private health information related to a plurality of consumers, where the private health information is used to identify and select a group of the consumers as suitable to receive promotional information related to the financial product or service, and providing the financial product or service to at least one member of the select group of consumers.

BRIEF DESCRIPTION OF THE DRAWINGS

While the appended claims set forth the features of the present invention with particularity, the invention and its advantages are best understood from the following detailed description taken in conjunction with the accompanying drawings, of which:

DETAILED DESCRIPTION OF THE INVENTION

The following examples further illustrate the invention but, of course, should not be construed as in any way limiting its scope.

Figure 1:
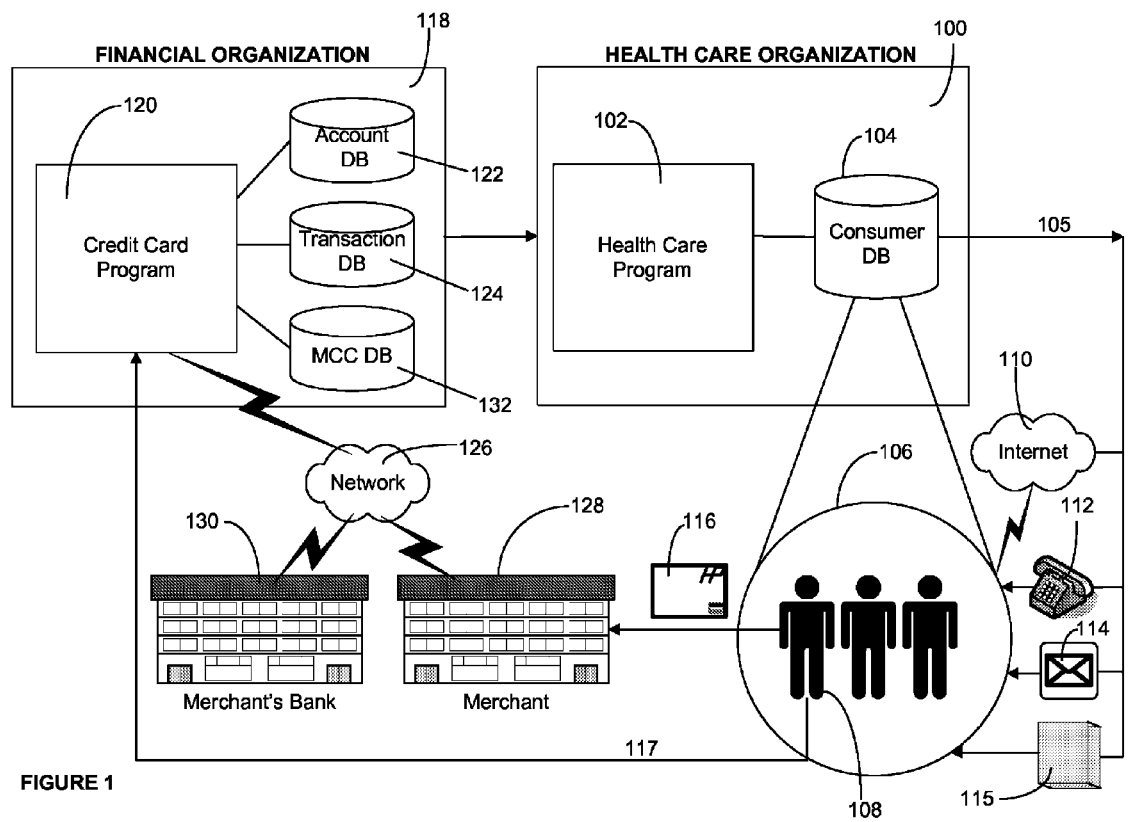
FIG. 1 illustrates combined health care organization and financial organization environments, wherein the health care organization cooperates with the financial organization by promoting enrollment and use of a financial product or service that includes terms having incentives for the use of the product or service in connection with health care, as contemplated by an embodiment of the present invention.

Turning to FIG. 1, an implementation of a system contemplated by an embodiment of the invention is shown with reference to a combined health care organization and financial organization environments. In one embodiment, the health care organization (HCO) 100 is an insurance company that administers a health care program 102, which preferably is a health insurance plan. Alternatively or in addition, the health care program 102 includes disability, life, dental, vision, pharmacy, behavioral health, or long-term care benefits, and combinations thereof. In the course of administering the health care program 102, the HCO 100 accumulates data within a consumer database 104. Since the consumer database 104 is used in connection with provision of health care services, it may contain private health information (PHI) subject to protection under the applicable laws and regulations, such as the Health Insurance Portability and Accountability Act (HIPAA) for example. Thus, consumer database 104 may include, but is not limited to, such information as name, address, age, sex, and other demographic and personal information as well as health records, such as, but not limited to, claims data, specific to a given health care consumer and collected in the process of administering a health care program 102 to the consumer.

In order to improve health and wellness and to alleviate increasing costs of medical expenses for its consumers, the HCO 100 cooperates with the financial organization 118 by promoting enrollment and use of a financial product or service that includes terms having incentives for the use of the product or service in connection with health care. The financial organization 118 may be a bank. In the illustrated embodiment, the financial product or service is a credit card program 120 having at least one credit card 116, which includes an account with an interest rate that applies to balances carried on the account, and including one or more incentives to use the credit card 116 in connection with health care expenses. Other embodiments may include a loan or a similar financial product or service administered by the financial organization 118 and having favorable terms, such as a below-market interest rate, that apply to health care related expenses. To this end, the HCO 100 queries the database 104 and uses PHI to identify and select a group of health care consumers 106 suitable to receive promotional information 105 related to the credit card program 120. Preferably, the HCO 100 identifies a desired group of consumers 106 by selecting the records within the consumer database 104 that match a desired demographic. For example, the HCO 100 may set a minimum age limit to make sure that the promotional information about the credit card program 120 is transmitted only to adult consumers. Other embodiments involve targeting consumers having predetermined health-related characteristics, such as those consumers determined to benefit most from, or most likely to respond positively to, the promotional information. Once the HCO 100 identifies a group of consumers 106 that are suitable to receive the promotional information 105, the HCO 100 uses one or more of its channels of communication to transmit the promotional information 105 to the select group 106. In the illustrated embodiment, the HCO 100 transmits the promotional information 105 relating to the credit card program 120 via Internet channels 110, telephone channels 112, and mail channels 114. The Internet channels of communication 110 may include websites, such as secure areas of the HCO 100 website where a personal login is required to view the secured information, as well as email notifications regarding the details of the credit card program 120. The telephone channels 112 may include HCO 100 call center referrals and other telephone contacts between HCO 100 and its consumers 106. Similarly, the mail channels 114 include explanation of benefits mailings, membership information mailings, and direct mail campaigns. Preferably, the HCO 100 also communicates the promotional information 105 by including it in member enrollment kits 115 transmitted to its consumers 106. Alternatively or in addition, the HCO 100 communicates the promotional information 105 to the general public by using public media channels, such as public areas of the HCO 100 website for example. However, it should be understood by those skilled in the art that the above description of various channels of communication between the HCO 100 and its consumers is for illustrative purposes only and other channels of communication may be used to transmit the promotional information 105. Preferably, the credit card program 120 is associated with the HCO 100 via a co-branding arrangement, whereby the promotional materials 105, as well as the credit card 116, include a logo of the HCO 100 and, optionally, other brand information related to the HCO 100.

Upon receipt of the promotional information 105, the consumer 108 applies for the credit card program 120 by sending a credit card application 117, which was included or referenced in the promotional information 105, to the financial organization 118 for processing. Upon approval of the application 117, the financial organization 118 assigns the consumer 108 an account number and stores the account details in an account database 122. The consumer 108 then uses the card 116 in connection with payment for any product or service, as long as the merchant 128 is compatible with the type of credit card network 126 through which the payment transactions using the card 116 must be processed. In embodiments, the credit card network 126 is a Visa network, a MasterCard network, a Discover network, or the like. The merchant's bank 130 receives the funds from the financial organization 118 when the financial organization 118 approves payment requests received from the merchant 128 via the network 126. The transaction database 124, in turn, is used to record all transactions associated with consumer's use of the card 116. The HCO 100 obtains revenue from the financial organization 118 based on consumer's 108 use of the credit card 116, where the revenue is preferably measured as, or is a function of, a predetermined percentage of consumer's 108 transaction amount. In an embodiment, the HCO 100 obtains additional revenue from the financial organization 118 based on new enrollments in the credit card program 120 coming from the selected group of consumers 106.

Although consumer 108 can use the credit card 116 to pay for any product or service, the card 116 includes special incentives to benefit the consumer 108 when the card 116 is used in connection with products or services related to health care. In one embodiment, upon approval of the transaction request, the financial organization 118 receives a merchant category code from the merchant 128 and queries the merchant category code database 132 to determine whether the code is associated with a category indicating that many or all products or services provided by the merchant 128 are related to health care. If so, the financial organization 118 applies one or more incentives to the transaction. In one embodiment, purchases made at national chain retail pharmacies, for example, which carry health care related products as well as a large number of non-health care related merchandise, may not be eligible for incentives. On the other hand, expenses incurred at specialty pharmacies or other merchants specializing in health care products or services, as well as at health care providers, would be eligible for the health care incentives. Other embodiments include applying incentives on a product, rather than merchant, level. Generally, examples of health care related products or services include, but are not limited to, health club membership fees, payments to medical providers for portions of medical expenses not covered by consumer's health, dental, or vision insurance, medical drug purchases, purchases of exercise equipment, as well as purchases made at merchant locations associated with the health care merchant category codes discussed above.

Figure 2:
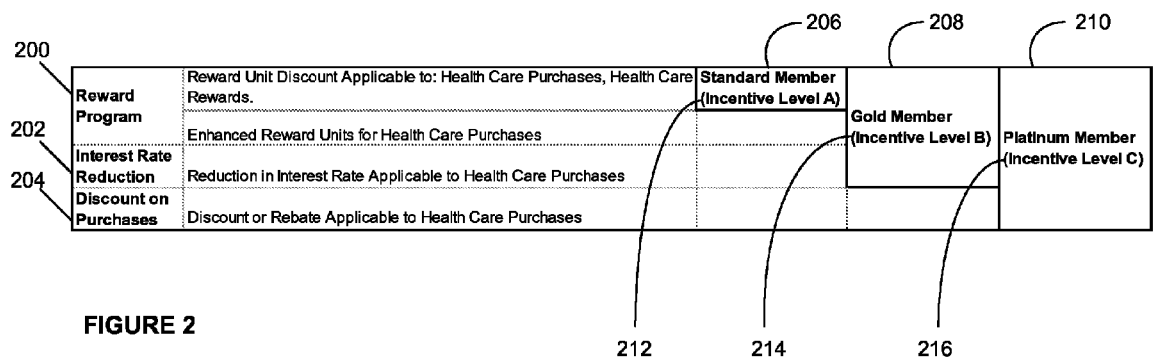
FIG. 2 is a chart illustrating health care related incentives included in a credit card program, in accordance with an embodiment of the invention.

Turning to FIG. 2, embodiments of the health care related incentives included in the credit card program 120 are illustrated. The incentives may include a reward program 200 where the consumer 108 earns reward units or points upon using the credit card 116 to make purchases. Accumulated reward units are subsequently used for redeeming rewards, such as merchandise or gift certificates, from a catalog published by the financial organization 118. In one embodiment, the reward program 200 includes a reward unit discount allowing the consumer 108 to reduce the amount of accumulated reward units necessary for redeeming merchandise when such reward units are earned in connection with health care related purchases. For example, upon using the card 116 to make a $100 payment for hospital expenses, the consumer 108 earns 100 reward units. Since these reward units are earned in connection with health care related expenditures, the consumer 108 needs only 90 reward units to redeem catalog rewards valued at 100 reward units. Preferably, a reward unit discount also applies when the consumer 108 is redeeming rewards that are related to health care. That is, in the above example, the consumer 108 is able to apply a further reward unit discount when redeeming a health club pass reward, for example. Another embodiment of a reward program 200 includes a provision that increases the number of reward units awarded in connection with the purchase of products or services related to health care as compared to non-healthcare related purchases. For example, the consumer 108 earns a 100 reward units for spending a $100 at a grocery store and 110 reward units for using the credit card 116 to pay a $100 dental bill.

Similarly, the incentives may include an interest rate reduction 202 applicable to charges generated by paying for health care products or services. In this embodiment, the health care related charges are itemized separately in order to compute a finance charge based on the reduced interest rate. In yet another embodiment, the financial organization 118 applies a predetermined discount 204 applicable to health care related purchases. The discount 204 may take the form of a predetermined percent discount or a cash rebate based on a total amount of health care related charges. While the credit card program 120 includes at least one of the health care incentives 200-204, preferably, the incentives are applied based upon a card membership level. In this case, one or more incentives 200-204 apply to a given member type 206-210 according to his or her corresponding incentive level 212-216. For example, a "standard" card membership 206 includes any one of the incentives 200-204 applicable at the corresponding incentive level 212, labeled "Incentive Level A." Similarly, a "gold" card membership 208 includes a combination of any two of the incentives, such as the reward program 200 and an interest rate reduction 202, where the incentives 200, 202 are applicable at a higher incentive level 214, labeled "Incentive Level B," than corresponding incentives for the standard card membership 206. Further, the "platinum" membership 210 may combine all incentives 200-204 applicable at the highest incentive level 216, labeled "Incentive Level C." Other incentive combinations are possible, such as where each card membership 206-210 includes all of the incentives 200-204, albeit applicable at different incentive levels 212-216. In such an embodiment, the interest rate reduction 202, for example, while applicable to all card membership types 206-210, provides the highest reduction to platinum members 210 (e.g., a 100 basis point reduction) versus standard members 206 (e.g., a 25 basis point reduction).

Figure 3:
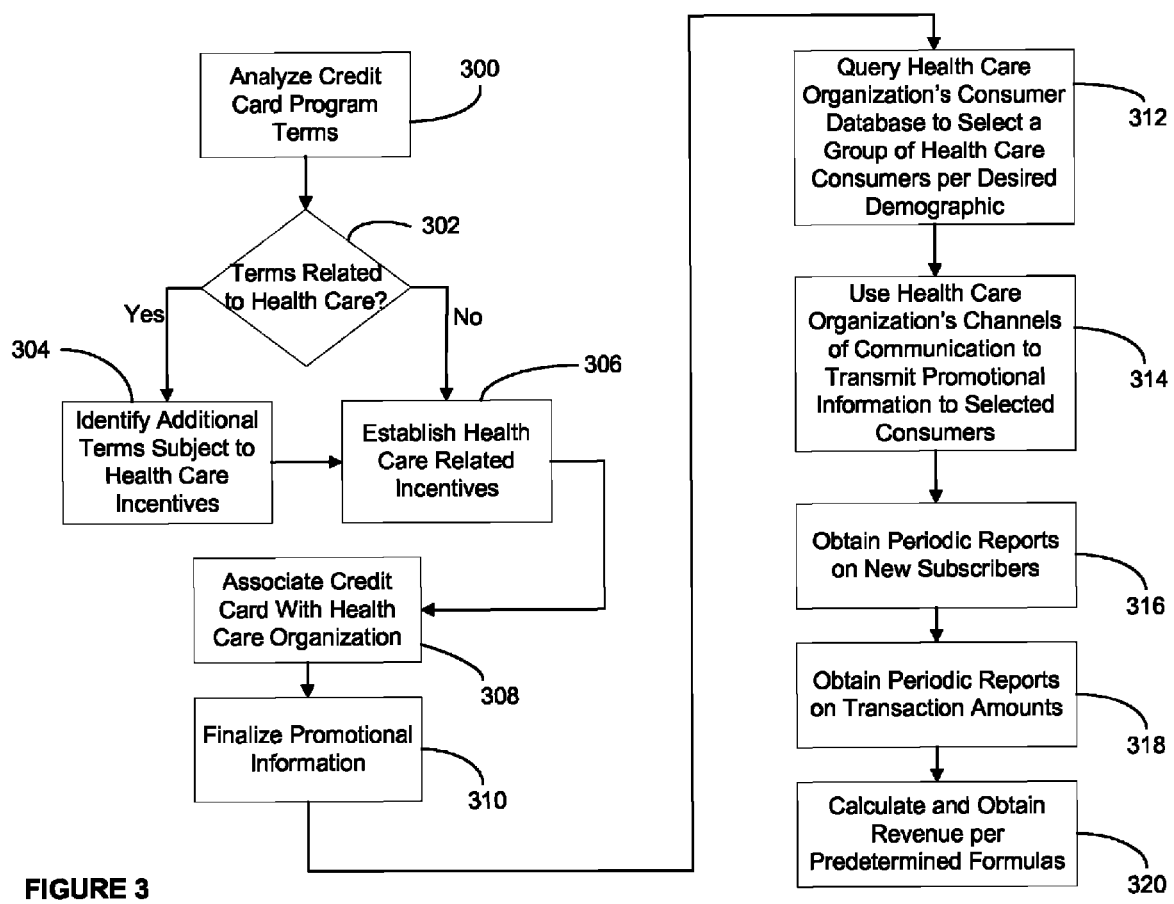
FIG. 3 is a flowchart illustrating a method performed in connection with promoting a credit card program, in accordance with an embodiment of the invention.

Turning to FIG. 3, an embodiment of a method performed in connection with promoting a credit card program 120 is illustrated. Initially, the HCO 100 and/or the financial organization 118 analyze 300 the terms of an existing credit card program to determine 302 whether at least one term of the program relates to health care, such as by having any of the health care related incentives similar to those discussed above in connection with FIG. 2. If one or more health care related terms are identified, the HCO 100 and/or financial organization 118 identifies 304 additional terms which may be subject to incentives geared toward health care expenditures. For example, a restructuring of the credit card program's reward and interest rate programs may be necessary to incorporate some or all of the incentives 200-204. If no health care related terms are identified, new health care related terms are established 306 by adding incentives 200-204 to the credit card program. In the illustrated embodiment, once the health care related terms are established 306, the HCO 100 and the financial organization 118 associate 308 the credit card program 120 and, correspondingly, the credit card 116, with the HCO 100 by way of a co-branded arrangement where the credit card program is administered by the financial organization 118, while the credit card 116 and promotional materials 105 include the logo and, optionally other brand information, of the HCO 100, as well as of the financial organization 118. Next, once the promotional information 105 is finalized 310, the HCO 100 uses the desired consumer demographic to query 312 its consumer database 104 to select a group of health care consumers 106 suitable to receive the promotional information 105. To enhance consumer privacy, the HCO 100 includes only the minimum necessary information regarding individual consumers into the selected data set. For example, in one embodiment, the HCO 100 uses only the information regarding the desired demographics, such as name, address, and age, to select the group of consumers 106. Next, in step 314, the HCO 100 uses its channels of communication 110-115 to transmit the promotional information 105 to the select group 106. In step 316, the HCO 100 obtains from the financial organization 118 periodic reports on new enrollments into the credit card program 120 from the group 106. The financial organization 118 compiles these reports based on the information contained in the account database 122 (FIG. 1). Similarly, in step 318, the HCO obtains from the financial organization 118 periodic reports on transaction amounts generated by subscribers within the selected group of consumers 106. The periodic transaction reports are generated by the financial organization 118 based on the information accumulated in the transaction database 124 (FIG. 1) during administration of the credit card program 120. Finally, in step 320, the HCO uses the periodic reports 316, 318 as inputs to predetermined formulas to calculate and obtain revenue from the financial organization 118.

Figure 4:
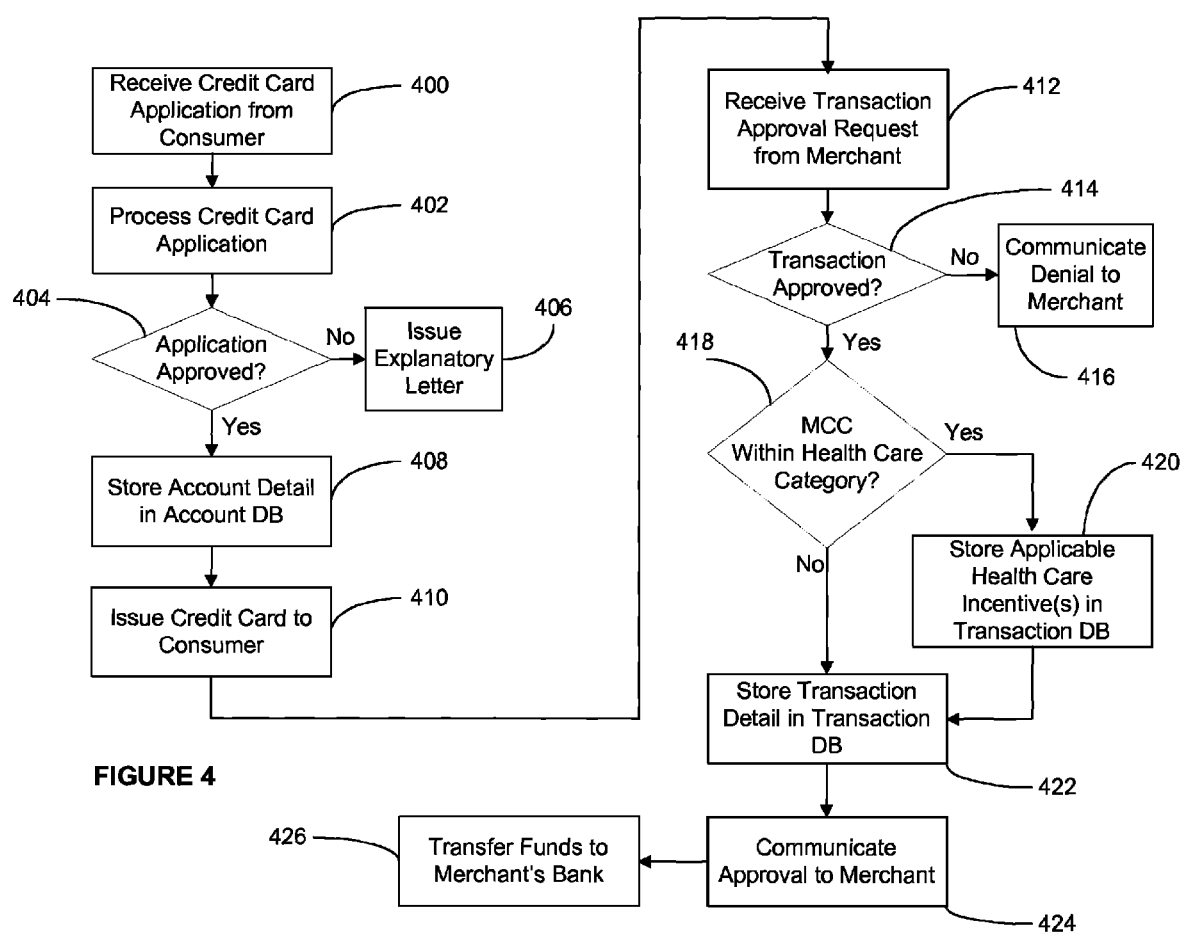
FIG. 4 is a flowchart illustrating a method of commercializing and administering a credit card program by a financial organization, in accordance with an embodiment of the invention.

Turning to FIG. 4, an embodiment of a method of commercializing and administering a credit card program 120 by the financial organization 118 is illustrated. After the HCO 100 transmits the promotional information 105 to the selected group of consumers 106, the financial organization 118 receives 400 a credit card application from one of the consumers 108 and processes 402 the application by evaluating 404 creditworthiness of the consumer 108 based on industry standards. If the financial organization 118 is not able to issue a credit card 116 to the consumer, it issues 406 an explanatory letter to the consumer. Otherwise, the financial organization 118 creates a new credit card account, categorizes the account into at least one membership category discussed above in connection with FIG. 2, stores 408 the account information in the account database 122, and issues 410 the credit card 116 to the consumer 108. Once the consumer 108 decides to use the credit card 116, the financial organization 118 receives 412 a transaction approval or payment request from the merchant 128 and processes 414 the approval request. If the transaction is not approved, the financial organization 118 communicates 416 a denial to the merchant 128. Otherwise, the financial organization queries the merchant category code (MCC) database 132 to determine 418 whether the MCC code associated with the merchant 128 is within one of a plurality of predetermined MCC codes related to merchants that specialize in health care products or services. Preferably, multiple industry categories are combined to form each health care merchant category, which is then assigned an MCC code. Exemplary health care merchant categories include specialty drug stores and pharmacies, dental and medical equipment and supplies, medical service providers, including dentists and opticians, nursing and personal care facilities, hospitals, health and beauty spas, vitamin stores, fitness centers, and the like. If an MCC code associated with the merchant 128 falls within one of the health care code categories, the financial organization 118 stores 420 one or more applicable health care incentives 200-204 associated with the transaction in the transaction database 124, in addition to storing 422 other detail related to the transaction. In an embodiment, the financial organization 118 determines applicability of health care incentives 200-204 on a product or service level. Next, in step 424, the financial organization 118 communicates 424 the approval to the merchant 128 and transfers 426 the requested funds to the merchant's bank 130.

Other embodiments of the invention include combining the benefits and incentives under the card 116 with a Medicare card used to pay for the products and services eligible to be covered under the consumer's 108 Medicare plan. In this case, the health care incentives under the card 116 apply to the portion of the health care and wellness expenditures that is not covered by Medicare.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method performed in connection with promoting a credit card program by a person or organization in possession of private health information related to a plurality of consumers, the credit card program having at least one credit card having an account with an interest rate that applies to balances carried on the account, the method comprising:
   determining that at least one term of the credit card program relates to health care, the term comprising incentives for use of the credit card program in connection with products or services related to health care, the incentives selected from the group consisting of:
   (a) a reward program having a reward unit discount that applies for redeeming rewards for the products or services related to health care,
   (b) a reduction in the interest rate when the credit card is used to pay for the products or services related to health care,
   (c) a discount that applies when the credit card is used to pay for the products or services related to health care, and
   (d) a reward program that awards reward units in connection with consumer purchases and having a provision that increases the number of reward units awarded in connection with the purchase of products or services related to health care;
   using the private health information to identify and select a group of the consumers as suitable to receive promotional information related to the credit card program; and
   transmitting the promotional information to consumers of the select group.

2. The method of claim 1 wherein the incentives comprise a combination of any two of:
   (a) the reward program having the reward unit discount that applies for redeeming rewards for the products or services related to health care;
   (b) the reward program that awards reward units in connection with consumer purchases and having the provision that increases the number of reward units awarded in connection with the purchase of products or services related to health care;
   (c) the reduction in the interest rate; and
   (d) the discount.

3. The method of claim 1 wherein the credit card program is associated with a health care organization.

4. A method performed in connection with promoting a financial product or service by a person or organization in possession of private health information related to a plurality of consumers, the method comprising:
   determining that the financial product or service has terms that have a substantial relationship to health-related products or services, the terms comprising incentives for the use of the financial product or service in connection with products or services related to health care;
   using the private health information to identify and select a group of the consumers as suitable to receive promotional information related to the financial product or service; and
   transmitting the promotional information to consumers of the select group;
   wherein the incentives comprise a reward program that awards reward units in connection with consumer purchases and having a provision that increases the number of reward units awarded in connection with the purchase of products or services related to health care.

5. The method of claim 4 wherein the financial product or service is associated with a health care organization.

6. The method of claim 4 wherein the financial product or service is a credit card having an account with an interest rate that applies to balances carried on the account.

7. The method of claim 6 wherein the terms include incentives comprising a reduction in the interest rate when the credit card is used in connection with the purchase of products or services related to health care.

8. The method of claim 7 wherein the incentives further include a reward program having a reward unit discount provided to the consumers for redeeming rewards for health care related products or services.

9. The method of claim 4 wherein the private health information comprises the consumers' name and address information.

10. The method of claim 4 wherein the promotional information is transmitted through at least one of mail, electronic mail, telephone, website, and a healthcare organization enrollment kit.

11. The method of claim 4 wherein the incentives further comprise a reward program having a reward unit discount provided to the consumers for redeeming rewards for the products or services related to health care.

12. The method of claim 4 wherein the incentives comprise a discount provided to the consumers when the financial product or service is used in connection with the purchase of the products or services related to health care.

13. The method of claim 4 wherein the terms include incentives that apply when the consumers use the financial product or service in connection with the purchase of products or services from a merchant belonging to one or more predetermined health care related merchant categories.

14. The method of claim 4 wherein the financial product or service comprises a Medicare card used in connection with the purchase of products or services that are eligible to be covered under a Medicare insurance plan.

15. The method of claim 14 wherein the terms comprise incentives for the use of the Medicare card in connection with products or services related to health care, and wherein the incentives apply to purchases of the products or services not covered under the Medicare insurance plan.

16. A method of commercializing a credit card program having at least one credit card, the credit card having an account with an interest rate that applies to balances carried on the account, the method comprising:
   establishing terms for the credit card program, at least one of the terms relating to health care and comprising incentives for the use of the credit card in connection with products or services related to health care, wherein the incentives are selected from the group consisting of:
- (a) a reward program having a reward unit discount that applies for redeeming rewards for the products or services related to health care;
- (b) a reduction in the interest rate when the credit card is used to pay for the products or services related to health care;
- (c) a discount that applies when the credit card is used to pay for the products or services related to health care; and
- (d) a reward program that awards reward units in connection with consumer purchases and having a provision that increases the number of reward units awarded in connection with the purchase of products or services related to health care;

offering the credit card program to be promoted by a person or organization that is in the possession of private health information related to a plurality of consumers, where the private health information is used to identify and select a group of the consumers as suitable to receive promotional information related to the credit card program; and providing the credit card to at least one member of the select group of consumers.

17. A non-transitory computer readable medium having stored thereon computer executable instructions executing a method performed in connection with promoting a credit card program by a person or organization in possession of private health information related to a plurality of consumers, the credit card program having at least one credit card having an account with an interest rate that applies to balances carried on the account, the instructions comprising:

determining that at least one term of the credit card program relates to health care, the term comprising incentives for use of the credit card program in connection with products or services related to health care, the incentives selected from the group consisting of:
- (a) a reward program having a reward unit discount that applies for redeeming rewards for the products or services related to health care,
- (b) a reduction in the interest rate when the credit card is used to pay for the products or services related to health care,
- (c) a discount that applies when the credit card is used to pay for the products or services related to health care, and
- (d) a reward program that awards reward units in connection with consumer purchases and having a provision that increases the number of reward units awarded in connection with the purchase of products or services related to health care;

using the private health information to identify and select a group of the consumers as suitable to receive promotional information related to the credit card program; and transmitting the promotional information to consumers of the select group.

18. The computer readable medium of claim 17 wherein the incentives comprise a combination of any two of:
- (a) the reward program having the reward unit discount that applies for redeeming rewards for the products or services related to health care;
- (b) the reward program that awards reward units in connection with consumer purchases and having the provision that increases the number of reward units awarded in connection with the purchase of products or services related to health care;
- (c) the reduction in the interest rate; and
- (d) the discount.

19. The computer readable medium of claim 17 wherein the credit card program is associated with a health care organization.

\* \* \* \* \*